(12) United States Patent
Wang

(10) Patent No.: US 6,991,600 B1
(45) Date of Patent: Jan. 31, 2006

(54) MALE SEXUAL AID

(76) Inventor: Hisn-Fu Wang, 9F, No.18, Sec.2, Gin-Shan South Road, Da-An District, Taipei (TW)

( * ) Notice: Subject to any disclaimer, the term of this patent is extended or adjusted under 35 U.S.C. 154(b) by 0 days.

(21) Appl. No.: 10/981,782

(22) Filed: Nov. 5, 2004

(51) Int. Cl.
*A61F 5/00* (2006.01)

(52) U.S. Cl. ...................................................... 600/38

(58) Field of Classification Search ............ 600/38–41; 128/842–844, 845
See application file for complete search history.

(56) References Cited

OTHER PUBLICATIONS

Xandria Collection 2002, p. 49.*

Xandria Collection 1997, p. 39.*

* cited by examiner

*Primary Examiner*—John P. Lacyk
(74) *Attorney, Agent, or Firm*—Dennison, Schultz, Dougherty & MacDonald

(57) ABSTRACT

A male sexual aid is made of soft and elastomeric material such as rubber, silicone rubber, or latex. The device is composed of a hollow tube and two rings arranged on two lateral sides thereof. The hollow tube (tubular cone body) has only one opening for accommodating a micro-vibrator or LED capsule. The two rings include a testis ring and a penis ring. In usage, the two rings respectively embrace the base of the testis and penis in parallel or crosswise so that the erected penis extends and lasts longer. Moreover, the hollow tube holds tightly on the top of the base of the penis so that the device stimulates or vibrates the clitoris of females for increasing sexual pleasure during intercourse.

32 Claims, 6 Drawing Sheets

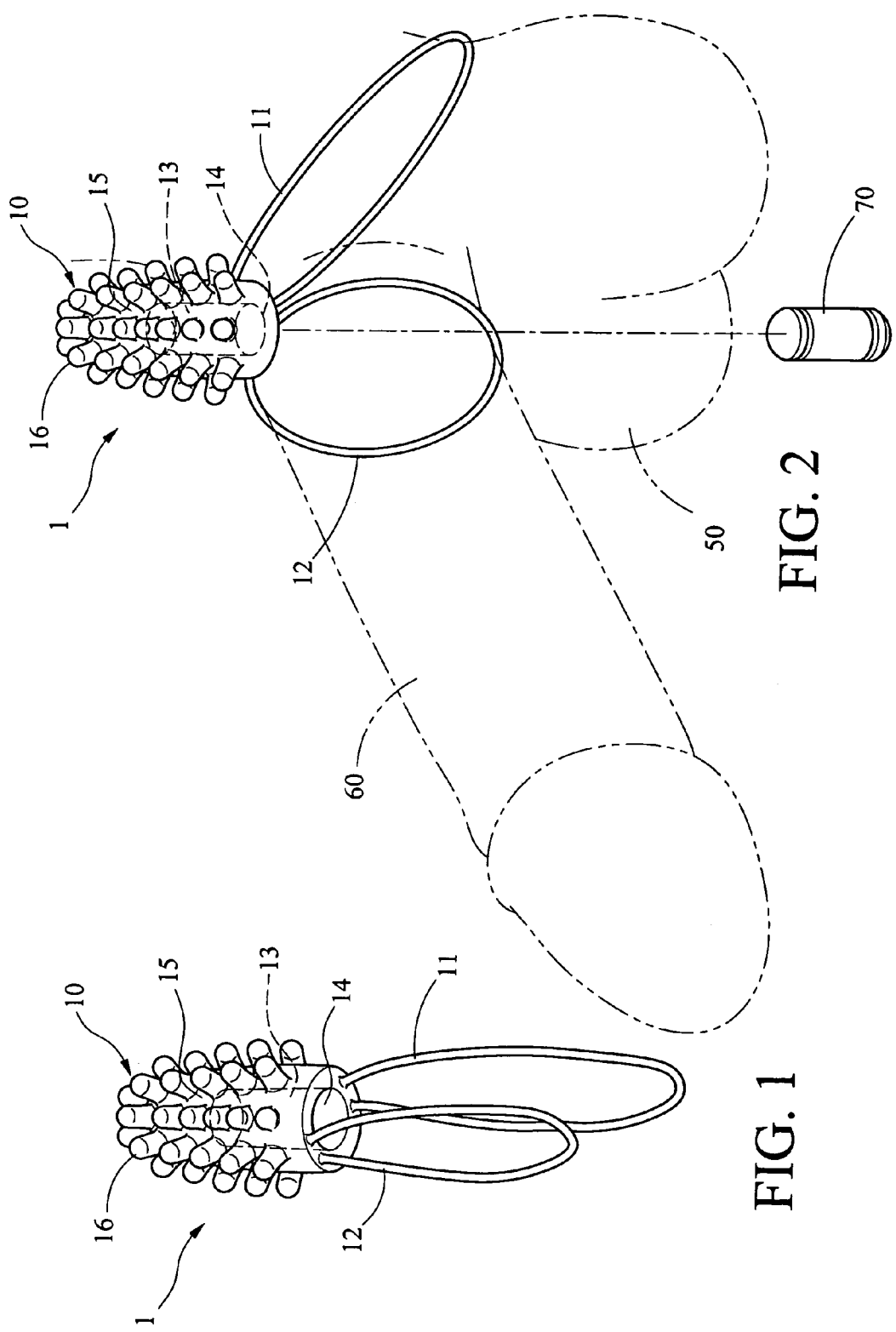

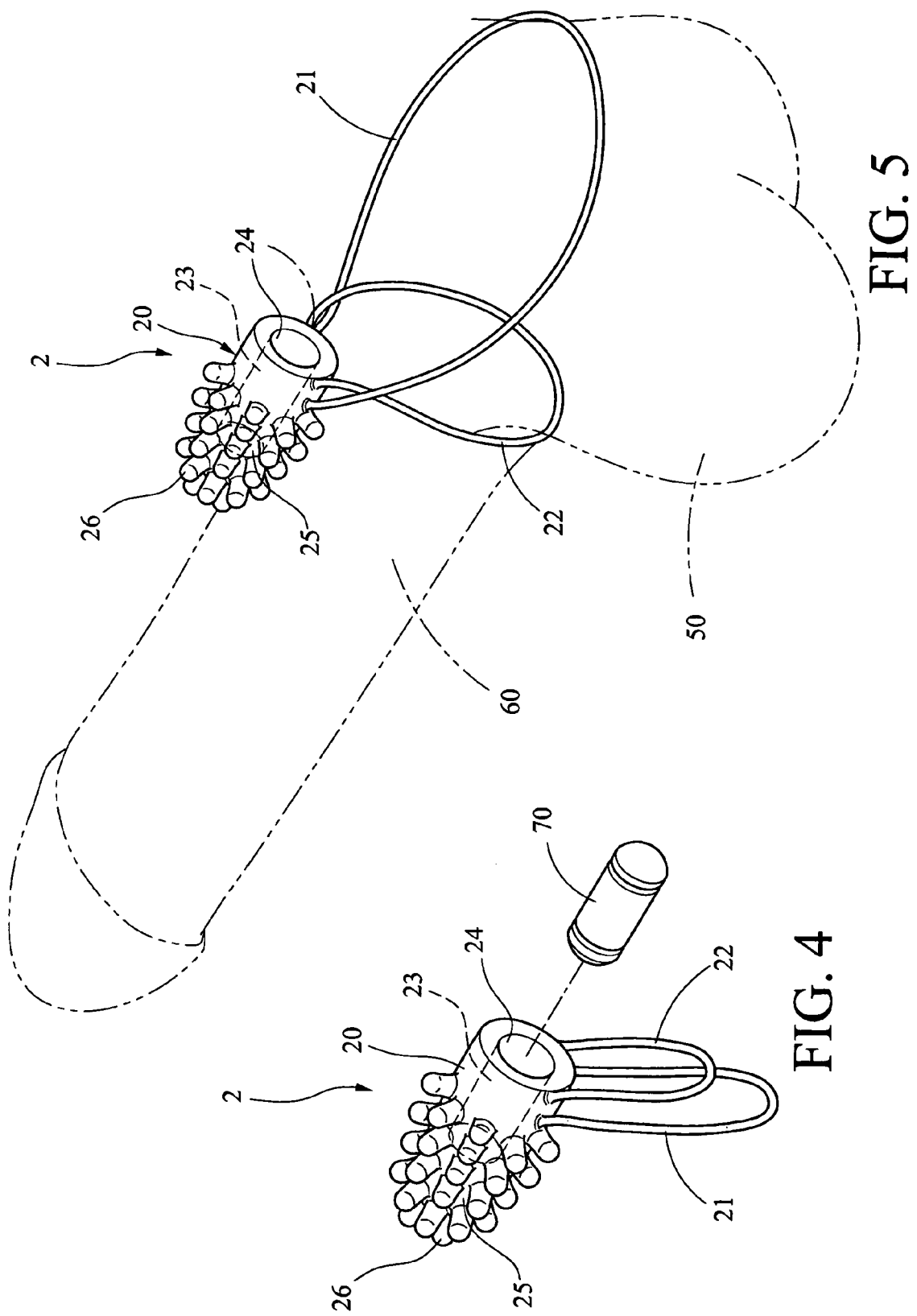

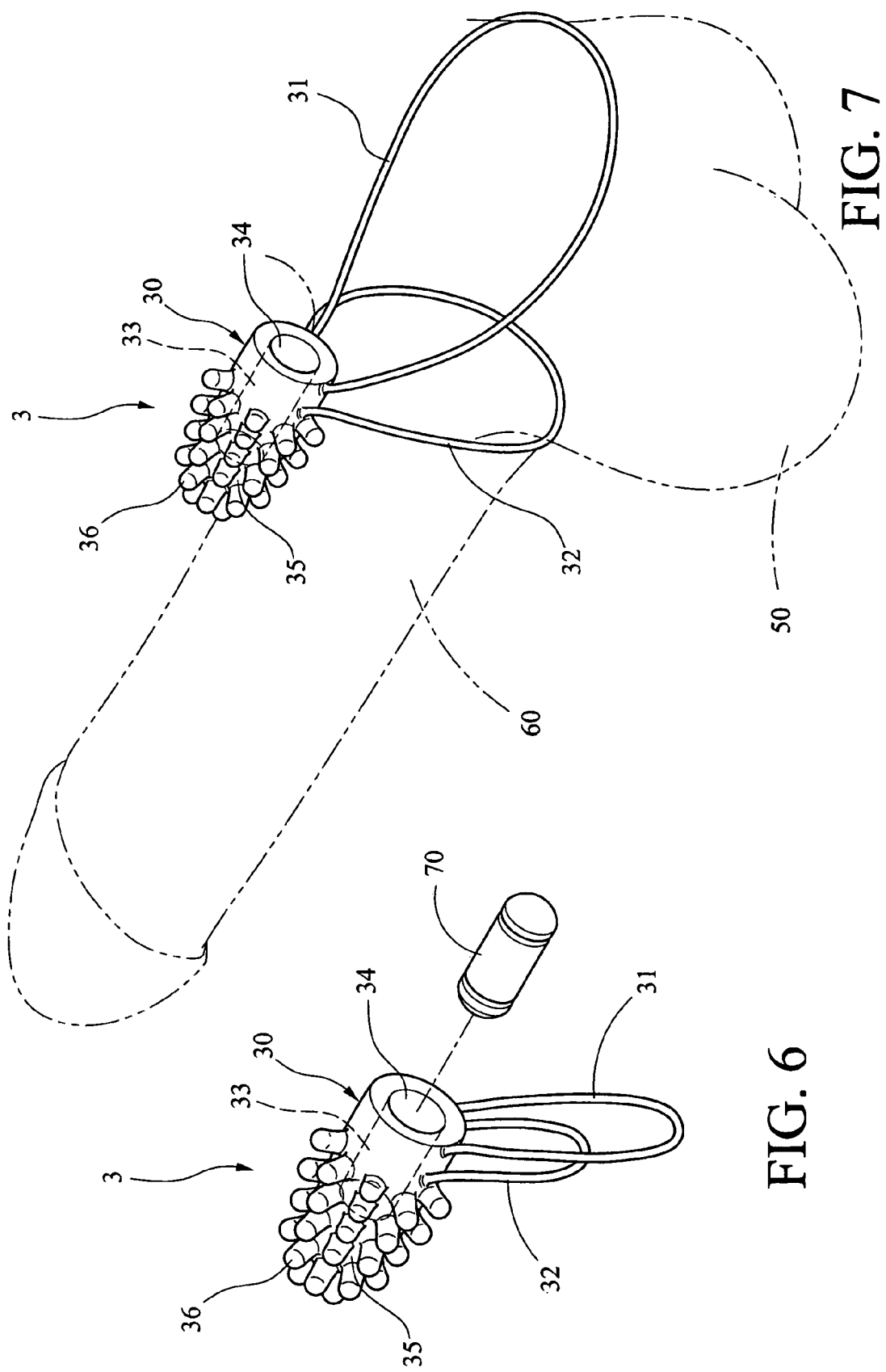

MALE SEXUAL AID

BACKGROUND OF THE INVENTION

The present invention relates to a sexual aid, especially to a male sexual aid having two rings holding firmly on the base of the penis and testis and a hollow cone body positioned on top of the base of the penis for contacting or vibrating the female clitoris. Thus the device can maintain the erection of penis and also stimulate the clitoris.

Making love is one of the most important things in lives for most of the people. Especially for men, they hope to keep best physical status during the intercourse process. However, with the increase of age or the change of physical condition, the penial erection may be affected. For example, a bulge on the belly or the base of the penis causes the relaxation of muscle and accordingly reduces the erect penis length. Moreover, the foreskin of the penis slides during intercourse. Thus the glans penis is covered by the foreskin and the condom is easy to fall off. There are a lot of sexual aids products available on the market now. For example, a vibration ring holds on the base of the penis or testis. The device includes a protrusion body on top of a ring. A vibrator is disposed inside the protrusion body so as to make the protrusion body stimulate the female clitoris. However, the device can't strain or support the penis backwards and thus can't show the full length of the erect penis. Furthermore, the design of the vibrating protrusion body doesn't match the ergonomics thus shows little effect on clitoral stimulation.

SUMMARY OF THE INVENTION

It is therefore a primary object of the present invention to provide a male sexual aid that is made of rubber, silicon rubber or latex. The invention is composed of a hollow tubular body and two ring disposed on the lateral side of the tubular body. The tubular body has a one-way opening for accommodating a micro-vibrator or a LED capsule therein. The two rings includes a ring for testis with a larger diameter and a ring for penis with smaller diameter. The rings hold the testis and the base of the penis in parallel or crossly so as to strain the penis backwards (towards the base part), show the full length of the erect penis, and increases the hardness and the perdurability of the penis. While the foreskin or the condom can also be embraced inside the ring for penis so as to avoid the problem of sliding or falling off. Moreover, the hollow tubular body is positioned on the base of the penis by the two rings so as to make one end of the tubular body without the opening contact with the clitoris. Therefore, the device has better effect on vibration or stimulation of the clitoris for increasing the sexual pleasure during intercourse.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein FIG. 1 is a perspective view of a first embodiment in accordance with the present invention;

FIG. 2 is a schematic diagram of the embodiment in FIG. 1 while being used;

FIG. 4 is a perspective view of a second embodiment in accordance with the present invention;

FIG. 5 is a schematic diagram of the embodiment in FIG. 4 while being used;

FIG. 6 is a perspective view of a third embodiment in accordance with the present invention;

FIG. 7 is a schematic diagram of the embodiment in FIG. 6 while being used;

DETAILED DESCRIPTION OF THE PREFFERED EMBODIMENT

The First Embodiment

Figure 3:
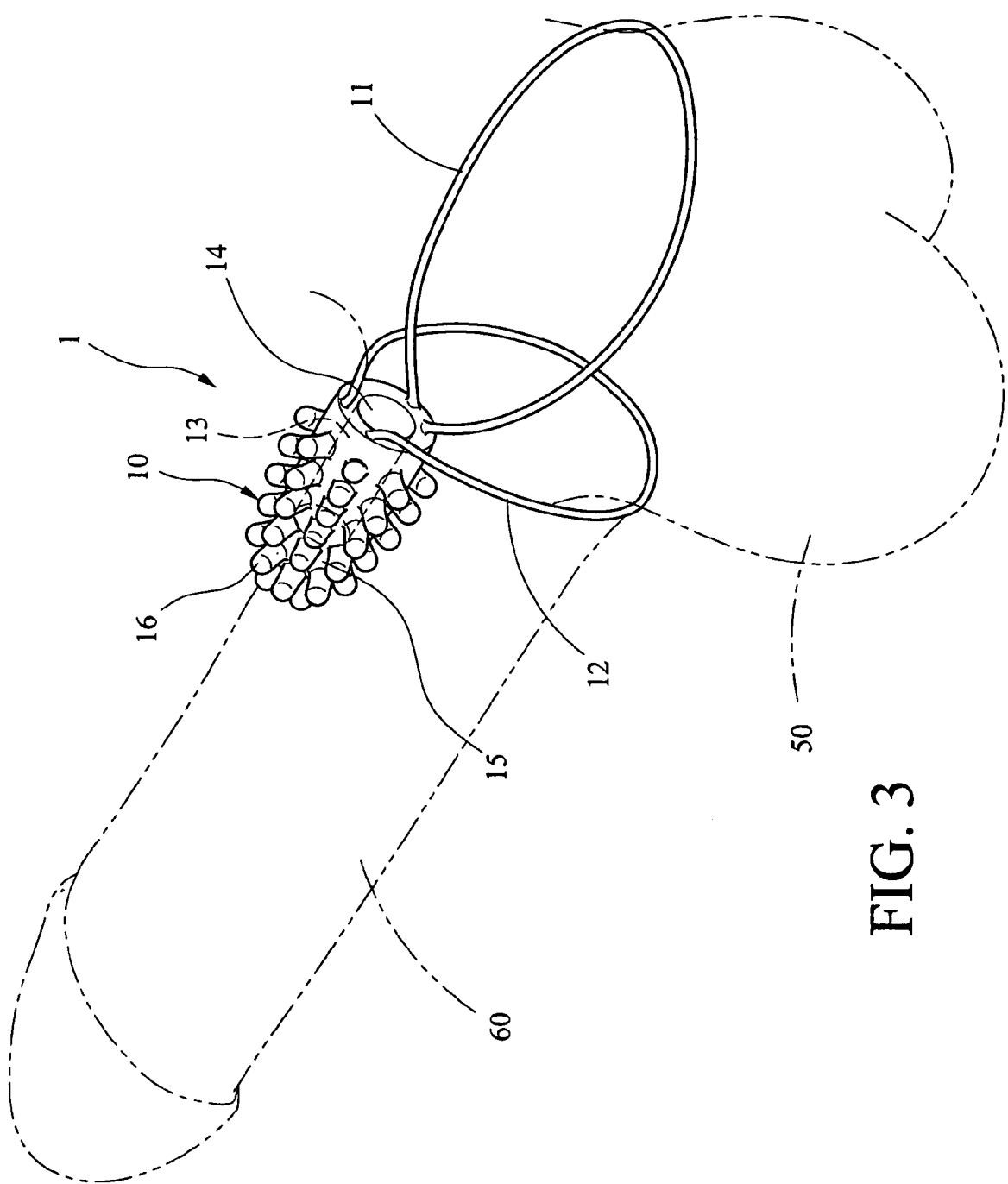
FIG. 3 is another schematic diagram of the embodiment in FIG. 1 while being used.

Refer to FIG. 1, the male sexual aid 1 in accordance with the present invention is made of soft and elastomeric material such as rubber, silicone rubber, or latex. The present invention is composed of a tubular body 10 and two rings 11, 12. The tubular body 10 is a cylindrical body, a cone body, a sphere-like body(such as three fourths the sphere), or the likes. A hollow space 13 is disposed inside the tubular body 10 and have only a one-way opening. According to users' needs, the hollow space 13 can be arranged with an accessory such as a micro-vibrator 70 or a LED capsule (not shown in figure). The two rings 11, 12 extends from the two lateral sides of the opening 14. One of them is a bigger ring (with larger diameter) for testis 11 while the other is a smaller ring for penis 12. While during manufacturing process, the two rings 11, 12 are made parallel to each other, arranged in perpendicular direction of the opening 14, as shown in FIG. 1.

There are two different ways of use. Refer to FIG. 2, the ring for testis 11 is on the rear (near the base of the penis) while the ring for penis 12 is on the front (towards the glans penis). The ring for testis 11 and the ring for penis 12 hold tightly the base of the testis 50 and penis 60 in parallel. Thus the tubular body 10 rises, being positioned on the top of the base of the penis 60 so as to make the opening 14 of the tubular body 10 faces downwards and covers on the base of the penis. Therefore, the items (such as micro-vibrator 70) inside the hollow space 13 or the surface of the opening 13 won't expose or contact the female organ and thus cause uncomfortable feelings. The ring for testis 11 strains the tubular body 10 and the ring for penis 12 backwards. Thus the full length of the erect penis is shown; the hardness and the perdurability of the penis also rise. Moreover, the foreskin or the condom is embraced by the ring for penis 12, won't fall off. Furthermore, the tubular body 10 is positioned on the base of the penis 60 so as to stimulate or vibrate the female clitoris.

Refer to FIG. 3, the other way is to put the ring for testis 11 on the front while the ring for penis 12 is set on the rear. The ring for testis 11 and the ring for penis 12 hold the testis 50 and the base of the penis 60 respectively. Then the tubular body 10 stands along the direction of the erect penis 60 and is positioned on top of the base of the penis 60. Thus the opening 14 of the tubular body 10 faces towards the human belly and the items (such as micro-vibrator 70) inside the hollow space 13 or the surface of the opening 14 won't expose or contact the female organ. The ring for testis 11 also strains the tubular body 10 and the ring for penis 12 backwards, the same as the first method. Therefore, this way of use for straining the penis 60 has better effect than the first method.

The Second Embodiment

Refer to FIG. 4, the present invention-male sexual aid 2 is made of soft and elastomeric material such as plastic rubber, silicon rubber or latex. The invention includes a tubular body 20 and two rings 21, 22, wherein the tubular body 20 is a cylindrical body, a cone body, a sphere-like body or the likes. A hollow space 23 is disposed inside the tubular body 20, with a one-way opening 24. According to users' needs, the hollow space 23 can be arranged with an accessory such as a micro-vibrator 70 or a LED capsule (not shown in figure). The two rings 21, 22 are disposed on the rear end of the tubular body 20, extending from one lateral side of the opening 24 in parallel. One of them is a bigger ring (with larger diameter) for testis 21 arranged on the front end while the other is a smaller ring for penis 22 on the rear end. While during manufacturing process, the two rings 11, 12 are made parallel to each other.

In usage, refer to FIG. 5, the ring for testis 21 and the ring for penis 22 hold the testis 50 and the base of the penis 60 respectively, cross each other. Then the tubular body 20 is parallel to the erect penis 60 and is positioned on top of the base of the penis 60. Thus the opening 24 of the tubular body 20 faces towards the belly and the items (such as micro-vibrator 70) inside the hollow space 23 or the surface of the opening 24 won't expose or contact the female organ. The ring for testis 21 for straining the testis 50 is used in the similar way as the embodiment shown in FIG. 3 has the similar effect on straining the penis 60.

The Third Embodiment

Refer to FIG. 6, a male sexual aid 3 in accordance with the present invention is made of soft and elastomeric material such as plastic rubber, silicon rubber or latex. The invention includes a tubular body 30 and two rings 31, 32, wherein the tubular body 30 is a cylindrical body, a cone body, a sphere-like body or the likes. A hollow space 33 is disposed inside the tubular body 30, with a one-way opening 34. According to users' needs, the hollow space 33 can be arranged with an accessory such as a micro-vibrator 70 or a LED capsule (not shown in figure). The two rings 31, 32 are disposed on the rear end of the tubular body 30, extending from one lateral side of the opening 34, parallel to each other. One of them is a bigger ring (with larger diameter) for testis 31 arranged on the rear end while the other is a smaller ring for penis 32 on the front end. While during manufacturing process, the two rings 31, 32 are made parallel to each other.

While being used, refer to FIG. 7, the ring for testis 31 and the ring for penis 32 hold the testis 50 and the base of the penis 60 respectively. Then the tubular body 30 is parallel to the erect penis 60 and is positioned on top of the base of the penis 60. Thus the opening 34 of the tubular body 30 faces towards the belly and the items (such as micro-vibrator 70) inside the hollow space 33 or the surface of the opening 34 won't expose or contact the female organ. The ring for testis 31 for straining the testis 50 is used in the similar way as the embodiment shown in FIG. 2 and has the similar effect on straining the penis 60.

The Forth Embodiment

Figures 8, 9:
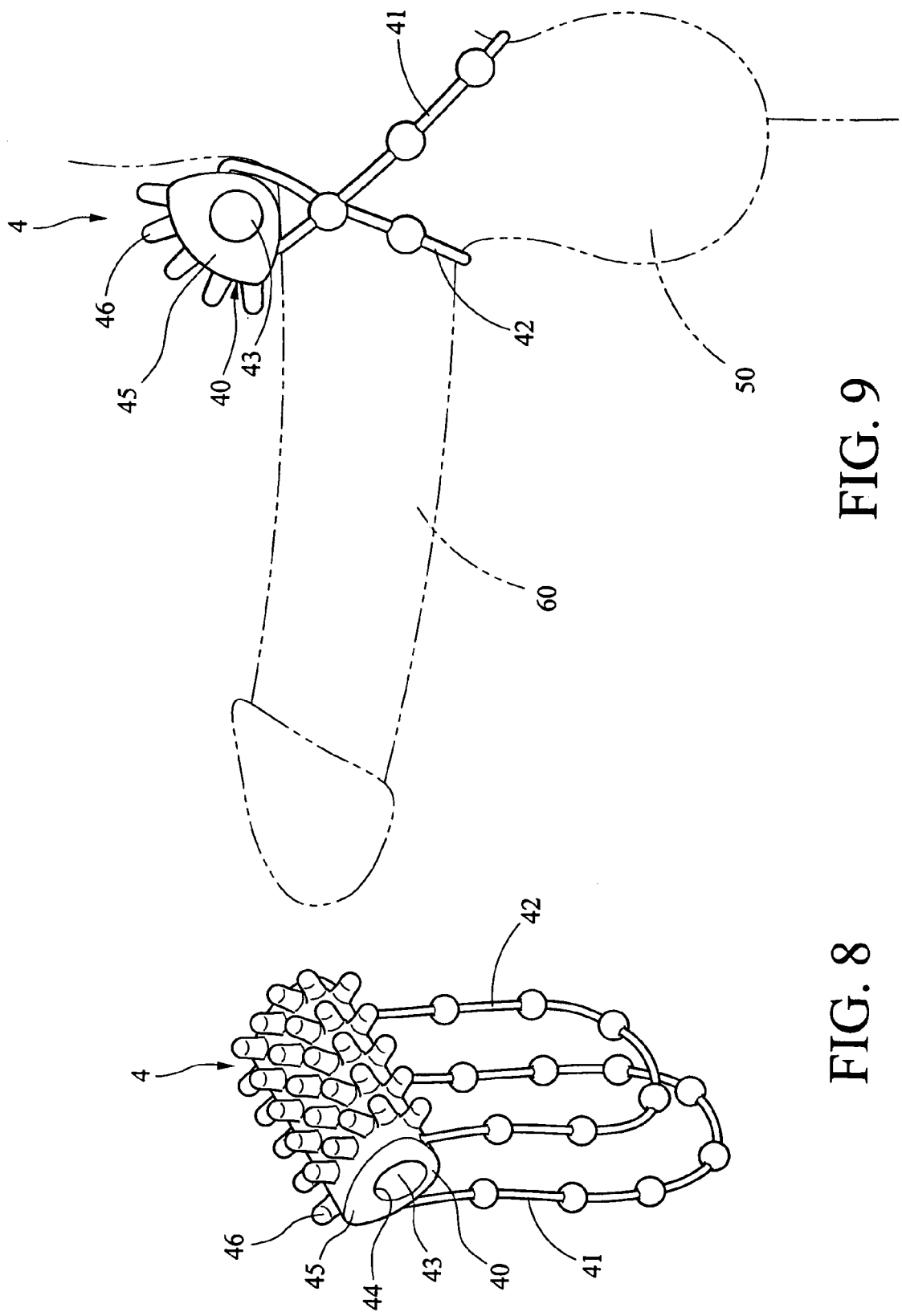
FIG. 8 is a perspective view of a fourth embodiment in accordance with the present invention.
FIG. 9 is a schematic diagram of the embodiment in FIG. 8 while being used.

Refer to FIG. 8, a male sexual aid 4 in accordance with the present invention is made of soft and elastomeric material such as plastic rubber, silicon rubber or latex. The invention includes a tubular body 40 and two rings 41, 42, wherein the tubular body 40 is a cylindrical body, a cone body, a sphere-like body or the likes. A hollow space 43 is disposed inside the tubular body 40, with a one-way opening 44. According to users' needs, the hollow space 43 can be arranged with an accessory such as a micro-vibrator 70 or a LED capsule (not shown in figure). The two rings 41, 42 are disposed on two lateral sides of the tubular body 40. One of them is a bigger ring (with larger diameter) for testis 41 while the other is a smaller ring for penis 42. While during manufacturing process, the two rings 41, 42 are made parallel to each other.

The difference between the male sexual aid 4 and the male sexual aids 2, 3 is that the cross section of the rings for testis 21, 31 and penis 22, 32 is parallel to the openings 24, 34 of the tubular bodies 20, 30. While the cross section of the rings 41, 42 is perpendicular to the opening 44 of the tubular body 40. Therefore, when being used, the tubular bodies 20, 30 of the male sexual aids 2, 3 is coaxial to (with) the penis 60, and the tubular bodies 20, 30 lies on the top of the base of the penis 60. But the axis of the male sexual aid 4 is perpendicular to the axis of the penis 60 so that the tubular body 40 reclines on the top of the base of the penis 60.

Figure 10:
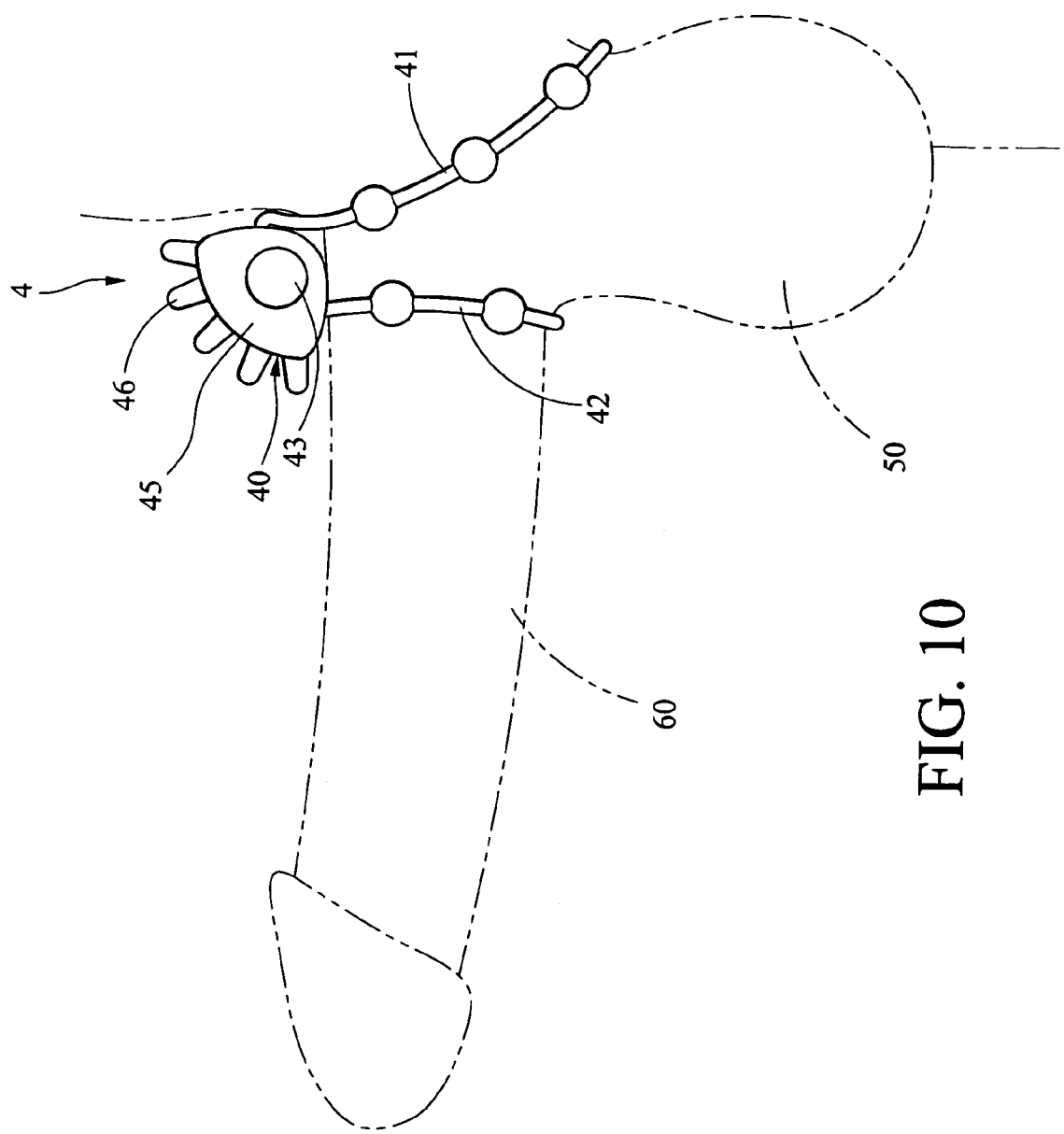
FIG. 10 is another schematic diagram of the embodiment in FIG. 8 while being used.

When being used, the male sexual aid 4 has two different ways of usage. Refer to FIG. 9, the ring for testis 41 on the front end and the ring for penis 42 on the rear end hold the testis 50 and the base of the penis 60 crossly. The other way is shown in FIG. 10, the ring for testis 41 on the rear end and the ring for penis 42 on the front end hold the testis 50 and the base of the penis 60 in parallel respectively. Then the tubular body 40 reclines on the top of the base of the penis 60.

Thus the opening 44 of the tubular body 40 faces towards the right or the left sides thereof so as to avoid the contact between the opening 44 and the female organ that may cause uncomfortable feelings. The ring for testis 41 for straining the testis 50 is used in the similar way as the embodiments of the male sexual aid 2, 3 shown in FIGS. 5, 7 and has the similar effect on straining the penis 60.

Moreover, the shape of the ring for testis 11, 21, 31, 41 and the shape of the ring for penis 12, 22, 32, 42 are not limited to a circle, they can also be elliptical, stilliform or other forms. As shown in FIG. 8, a plurality of granules are disposed on the rings so as to increase the binding force or modify the appearance.

In addition, the tubular body 10, 20, 30, 40 contacts the clitoris. The shape of the tubular body 10, 20, 30, 40 can be a cylindrical body, a cone body, a sphere-like body or the likes. The thickness of the front end 15, 25, 35, 45 of each tubular body or the surface of each tubular body can be increased so as to properly stimulate the female clitoris. Furthermore, a plurality of soft elastic post 16, 26, 36, 46 is disposed on the surface of the tubular body 10, 20, 30, 40 so as to have better effect on clitoral stimulation. Especially when a micro-vibrator 70 is set inside the hollow space 16, 26, 36, 46, the stimulate effect of the thicker front end 15, 25, 35, 45 and the post 16, 26, 36, 46 are far more enhanced.

In usage, users can insert the foreskin or the condom inside the ring for penis 12, 22, 32, 42 for being fastened firmly. Therefore, the foreskin or the condom won't slide or fall off during intercourse and the effect of stimulation is also improved.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A male sexual aid made of soft and elastomeric material comprising a tubular body and two rings, wherein
    a hollow space is disposed inside said tubular body and having a one-way opening to form an opening to form an opening plane;
    said rings having a ring adapted for testis and a ring adapted for penis, extending from the two lateral sides of the opening plane on symmetrical position;
    if the ring adapted for testis is on the front end, the ring adapted for penis is on the rear end; if the ring adapted for penis is on the front end and the ring adapted for testis is on the rear end; the ring adapted for testis and the ring adapted for penis hold the testis and the base of the penis tightly in parallel or crossly; the tubular body rises, being positioned on top of the base of the penis so as to make the opening of the tubular body faces downwards and covers on the base of the penis or belly; thus the opening plane won't expose or contact the female organ.

2. The male sexual aid as claimed in claim 1, wherein the diameter of said ring for testis is longer than the diameter of said ring for penis.

3. The male sexual aid as claimed in claim 1, wherein the front end of said tubular body is thickened.

4. The male sexual aid as claimed in claim 1, wherein a plurality of post are disposed on the outer surface of said tubular body.

5. The male sexual aid as claimed in claim 1, wherein said soft elastomeric material is plastic rubber, silicon rubber or latex.

6. the male sexual aid as claimed in claim 1, wherein said ring for testis and said ring for penis are arranged perpendicular to said opening plane and parallel to each other.

7. The male sexual aid as claimed in claim 1, wherein a vibrator or light-emitting diode capsule is inserted into said hollow space of said tubular body through said opening.

8. The male sexual aid as claimed in claim 1, wherein said tubular body is a cylindrical body, a cone body, a sphere-like body.

9. A male sexual aid made of soft and elastomeric material comprising a tubular body and two rings, wherein
    a hollow space is disposed inside said tubular body and having a one-way opening to form an opening plane;
    said two rings having a ring adapted for testis on the front end of said tubular body and a ring adapted for penis on the rear end of said tubular body, both disposed on one lateral side of the rear end of said tubular body, parallel to said opening plane;
    the ring adapted for testis and the ring adapted for penis respectively hold the testis and the base of the penis in cross status; the tubular body is parallel to the erect penis and is positioned on top of the base of the penis so that the opening plane of the tubular body faces and covers the belly and the opening plane won't expose or contact the female organ.

10. The male sexual aid as claimed in claim 9, wherein the diameter of said ring for testis is longer than the diameter of said ring for penis.

11. The male sexual aid as claimed in claim 9, wherein the front end of said tubular body is thickened.

12. The male sexual aid as claimed in claim 9, wherein a plurality of post are disposed on the outer surface of said tubular body.

13. The male sexual aid as claimed in claim 9, wherein said soft elastomeric material is plastic rubber, silicon rubber or latex.

14. The male sexual aid as claimed in clam 9, wherein said ring for testis and said ring for penis are arranged parallel to said opening plane and parallel to each other.

15. The male sexual aid as claimed in claim 9, wherein a vibrator or a light-emitting diode capsule is inserted into said hollow space of said tubular body through said opening.

16. The male sexual aid as claimed in claim 9, wherein said tubular body is a cylindrical body, a cone body, a sphere-like body.

17. A male sexual aid made of soft and elastomeric material comprising a tubular body and two rings, wherein
    a hollow space is disposed inside said tubular body and having a one-way opening to form an opening plane;
    said two rings having a ring adapted for penis on the front end of said tubular body and a ring adapted for testis on the rear end of said tubular body, both disposed on one lateral side of the rear end of said tubular body, parallel to said opening plane;
    the ring adapted for testis and the ring adapted for penis respectively hold the testis and the base of the penis in parallel while the tubular body is parallel to the erect penis and is positioned on tip of the base of the penis so that the opening plane of the tubular body faces and covers a male's belly.

18. The male sexual aid as claimed in claim 17, wherein the diameter of said ring for testis is longer than the diameter of said ring for penis.

19. The male sexual aid as claimed in claim 17, wherein the front end of said tubular body is thickened.

20. The male sexual aid as claimed in claim 17, wherein a plurality of posts are disposed on the outer surface of the front end of said tubular body.

21. The male sexual aid as claimed in claim 17, wherein said soft elastomeric material is plastic rubber, silicon rubber or latex.

22. The male sexual aid as claimed in claim 17, wherein said ring for testis and said ring for penis are arranged parallel to said opening plane and parallel to each other.

23. The male sexual aid as claimed in claim 17, wherein a vibrator or a light-emitting diode capsule is inserted into said hollow space of said tubular body through said opening.

24. The male sexual aid as claim din claim 17, wherein said tubular body is a cylindrical body, a cone body or a sphere-like body.

25. A male sexual aid made of soft and elastomeric material comprising a tubular body and two rings, wherein
    a hollow space is disposed inside said tubular body and having a one-way opening to form an opening plane;
    said two rings having a ring adapted for penis and a ring adapted for testis, both disposed on two lateral sides of said tubular body, perpendicular to said opening plane;
    if the ring adapted for testis is on the front end, the ring adapted for penis is on the rear end; if the ring adapted for penis is on the front end and the ring adapted for testis is on the rear end; the ring adapted for testis and the ring adapted for penis respectively hold the testis and the base of the penis tightly in parallel or crossly; the tubular body reclines, being positioned on top of the base of the penis so as to make the opening of the tubular body faces the right or the left sides.

26. The male sexual aid as claimed in claim 25, wherein the diameter of said ring for testis is longer than the diameter of said ring for penis.

27. The male sexual aid as claimed in claim 25, wherein the front end of said tubular body is thickened.

28. The male sexual aid as claimed in claim 25, wherein a plurality of post are disposed on the outer surface of the front end of said tubular body.

29. The male sexual aid as claimed in claim 25, wherein said soft elastomeric material is plastic rubber, silicon rubber or latex.

30. The male sexual aid as claimed in claim 25, wherein said ring for testis and said ring for penis are arranged parallel to each other.

31. The male sexual aid as claimed in claim 25, wherein a vibrator or a light-emitting diode capsule is inserted into said hollow space of said tubular body through said opening.

32. The male sexual aid as claimed in claim 25, wherein said tubular body is a cylindrical body, cone body or a sphere-like body.

* * * * *